Aug. 18, 1959 F. SPANBAUER Plant Pat. 1,860
ROSE PLANT
Filed Dec. 15, 1958
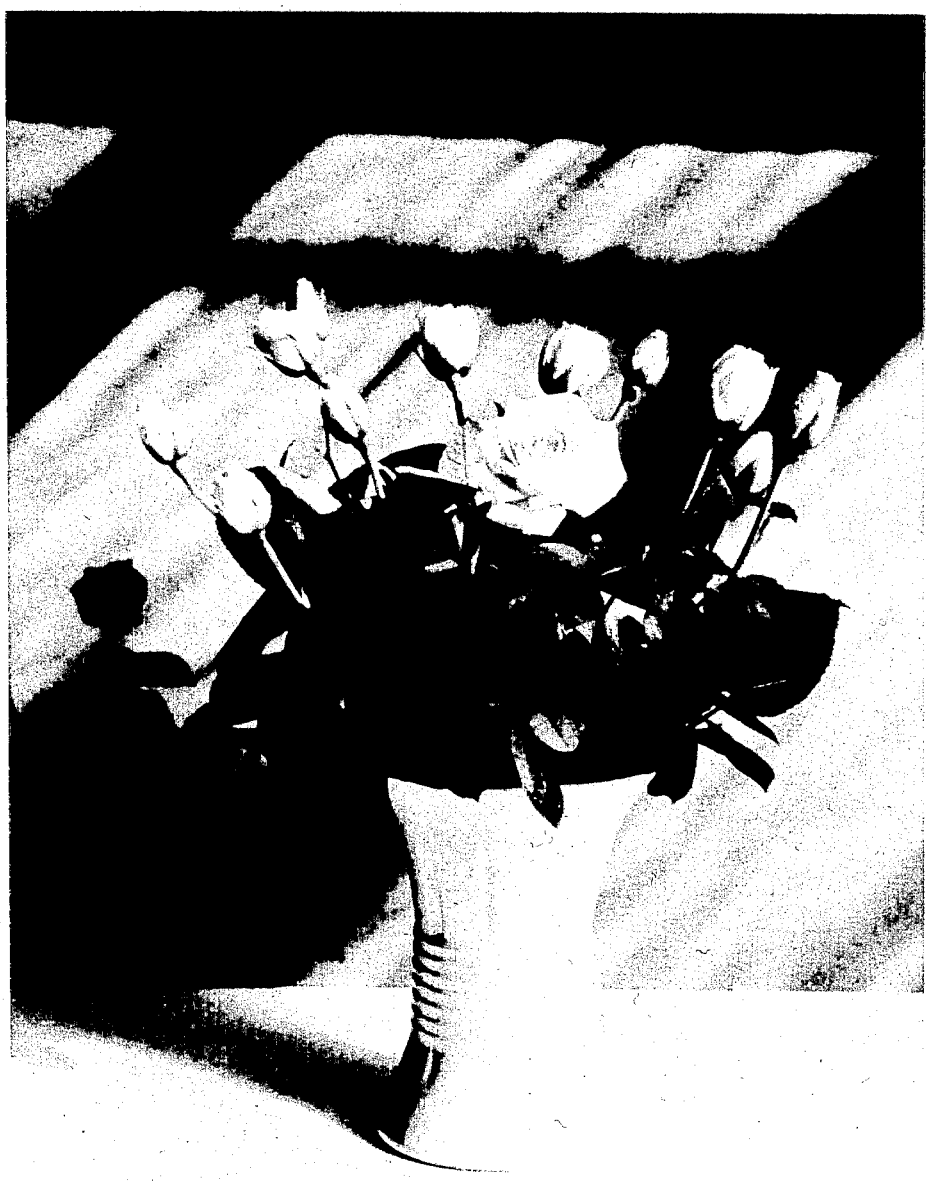
INVENTOR
Frank Spanbauer
BY Robert Robb
ATTORNEYS United States Patent Office Plant Pat. 1,860
Patented Aug. 18, 1959

1,860

ROSE PLANT

Frank Spanbauer, Decatur, Ill.

Application December 15, 1958, Serial No. 780,648

1 Claim. (Cl. 47—61)

The present invention relates to a new and distinct variety of rose plant of the polyantha class, which was originated by me as a selected cultivated seedling derived from an initial cross of "Cecile Brunner" (unpatented) with "Mrs. R. M. Finch," followed by further crossings of selected seedlings resulting therefrom, culminating in the selection of the present variety as an achievement of a new variety which is particularly characterized as to novelty by the following unique combination of characteristics which are outstanding in the new variety and which distinguish it from its parents as well as from all other varieties of which I am aware:

(1) An upright habit of growth;
(2) Excellence for cut flower production;
(3) Exceptionally fine qualities of the flowers;
(4) Long buds which are borne on vigorous and upright stems of medium length;
(5) A slow bud-opening habit and uniformity of color throughout the growing season;
(6) A distinctive Camellia Rose and Rose Opal general color tonality of the outer and inner surfaces, respectively, of the flower petals, which remains constant from the opening bud stage throughout the life of the blooms and including the dehydrated petal stage even when cut from the plant; and
(7) Exceptionally good keeping qualities of the flowers.

The original parent variety, "Mrs. R. M. Finch," has long been noted for its high flower production and long-lasting quality of the blooms, but the flowers thereof are borne on short stems, the stems and branches are very thorny, and the pink color in the mature flowers is not retained more than a few days. The variety "Cecile Brunner" is characterized by long buds, strong stems of medium length, good bud color, but the flowers are almost single in type, with many fewer petals than the flowers of "Mrs. R. M. Finch" or the present new variety. My new variety has only a few thorns in comparison with other varieties; its flowers are more consistently uniform in color from the bud stage to the mature bloom; and the color itself is distinct from that of the flowers of either variety aforementioned.

Asexual reproduction of my new variety, as performed by me by grafting in greenhouses at Decatur, Illinois, and also as performed by budding in outdoor fields at Carlton, Oregon, shows that the foregoing characteristics and distinctions come true to form and are established and transmitted through succeeding propagations.

The accompanying drawing shows typical specimens of the vegetative growth and flowers of my new variety, in different stages of development and as depicted in color as nearly true as it is reasonably possible to make the same in a color illustration of this character.

The following is a detailed description of the new variety, with color terminology in accordance with the British Horticultural Colour Chart, except where general color terms of ordinary dictionary significance are obvious:

Type: Hardy; bush; greenhouse and outdoor; seedling; for cut flowers and for garden decoration.
Class: Polyantha.
Breeding: Initial cross of "Cecile Brunner" × "Mrs. R. M. Finch," followed by further crossings of selected unnamed seedlings thereof, culminating in selection of the seedling which is the subject hereof.
Propagation: Holds its distinguishing characteristics through succeeding propagations by grafting and budding.

*Flower*

(Observations made from specimens grown in a greenhouse at Decatur, Illinois.)
Continuity: Continuous.
Frangrance: Slight in bud, but moderate when fully open. Nature—centifolia.
Flowers borne: Singly; on strong stems of medium length.
Quantity of bloom: Abundant, both in greenhouse and outdoors.
Bud:
*Peduncle.*—Medium length; medium caliper; erect; stiff; entirely smooth. Color—medium green.
*Before calyx breaks.*—Size—medium. Form—long; pointed; with a conspicuous neck; without foliaceous appendages on the surface of the bud; with slender, spear-like foliaceous parts extending beyond the tip of the bud equal to ¼ of its length. Color—Spinach Green, Plate 0960/3, page 187.
*As caylx breaks.*—Color—Camellia Rose, Plate 622/3, page 148.
*As first petal opens.*—Size—medium. Form—very long; pointed. Color: outside—Camellia Rose, Plate 622/2, page 148; inside—Rose Opal, Plate 022/3, page 110.
*Opening.*—Opens up well; is retarded from opening by cold and dry weather.
Bloom:
*Size (when fully open).*—Medium; from 2 inches to 3 inches.
*Petalage.*—Double (more petals but the stamens not hidden); from 40 to 45 petals; arranged regularly.
*Form.*—Full and high-centered at first, but becoming flat; petals at first being tightly rolled inward, but later becoming very loosely cupped outward at maturity.
Petals:
*Texture.*—Thick; leathery; with both inside and outside satiny.
*Shape.*—Outside—obovate, with 2 notches; outside petals are aobut twice the area of inside petals. Intermediate—obovate, with 2 notches. Inside—obovate, with 2 notches.

This description of a newly opened flower was made from a rose grown in a greenhouse in the month of October at Decatur, Illinois:

*Color.*—Outer petal: outside surface — Camellia Rose, Plate 622/2, page 148; inside surface—Rose Opal, Plate 022/3, page 110. Intermediate petal: Outside surface—Camellia Rose, Plate 622/2, page 148; inside surface—Rose Opal, Plate 022/3, page 110. Inner petal: outside surface—Camellia Rose, Plate 622/2, page 148; inside surface—Rose Opal, Plate 022/3, page 110. (Base of all petals is pale lemon in color.)

This description was made from a rose that was open for 3 days in a greenhouse in the month of October at Decatur, Illinois:

*Color.*—Outer petal: outside surface — Camellia Rose, Plate 622/2, page 148; inside surface—Rose Opal, Plate 022/3, page 110. Inner petal: outside surface—Camellia Rose, Plate 622/2, page 148; inside surface—Rose Opal, Plate 022/3, page 110. (Base of all petals is pale lemon in color.)

*General color effect.*—Newly opened flower—Rose Opal. 3-days open—Camellia Rose.

*Behaviour.*—Persist; retarded by cold and accelerated by heat; petals retain color even when dehydrated with age.

*Flower longevity.*—On bush in garden—from 7 to 10 days in October. Cut roses grown outdoors and kept at living-room temperatures—from 7 to 10 days in October. Cut roses grown in greenhouse and kept at living-room temperatures—from 7 to 10 days in October.

*Reproductive organs*

Stamens: Many; irregularly arranged about pistils. Color—pale creamish—almost white.

Filaments: Medium length; many with anthers. Color—almost white.

Anthers: Medium size; open at various times. Color—almost white.

Pollen: Moderate. Color—gold.

Pistils: Few.

Styles: Uneven; from medium length to long; heavy; bunched.

Stigma: Color—white.

Ovaries: All enclosed in calyx.

Hips: Globular; moderately smooth; walls thick and fleshy. Color—green at first, but later becoming brown.

Sepals: Permanent; long; spear-shaped; curled. Color—Spinach Green, Plate 0960/3, page 187.

Seeds: Few; medium size.

*Plant*

Foliage:

*Leaves.*—Compound of 5 leaflets; normal abundance; medium size; moderately heavy; leathery; glossy.

*Leaflets.*—Shape—from oval to elliptical, with apex acute. Base—obtuse. Margin—serrate.

*Color.*—Mature: upper surface—Spinach Green, Plate 0960/1, page 187; glossy and shiny; under surface—Spinach Green, Plate 0960/3, page 187; dull. Young: upper surface—Rhodonite Red, Plate 0022, page 188 on the outer marginal half, merging into Sap Green, Plate 62, page 62 which extends to center of main vein; shiny; under surface—Rhodonite Red, Plate 0022/2, page 188 on the outer marginal half, merging into Sap Green, Plate 62/2, page 62; dull.

*Rachis (the supporting stem of the compound leaf).*—Heavy. Upper side—smooth. Under side—sparsely thorny.

*Stipules.*—Moderately long; medium width; with moderately long points turning out at an angle of less than 45°.

*Disease resistance.*—Good resistance to mildew and blackspot as determined by comparison with other varieties grown under comparable cultural conditions at Decatur, Illinois.

*Insect resistance.*—Normal resistance to aphids and red spider mite, as determined by comparison with other varieties grown under comparable cultural conditions at Decatur, Illinois.

Growth:

*Habit.*—Bushy; much-branched.

*Growth.*—Vigorous.

*Canes.*—Medium caliper.

*Main stems.*—Color—bright green. Thorns—few; almost straight; slightly pointed downward; with long, narrow base; color — medium brown. Prickles—none. Hairs—none.

*Branches.*—Color — bright green. Thorns — few; long; almost straight; with long, narrow base; color—medium brown. Prickles—none. Hairs—none.

*New shoots.*—Color—bright red. Thorns — few; long; almost straight; color—from bright rosy pink at base to light beige at tip. Prickles—none. Hairs—none.

I claim:

A new and distinct variety of rose plant of the polyantha class, substantially as herein shown and described, characterized particularly as to novelty by the unique combination of an upright habit of growth, excellent cut flower production, exceptionally fine flower qualities, long buds borne on vigorous and upright stems of medium length, a slow bud-opening habit and uniform color throughout growing season, a distinctive Camellia Rose and Rose Opal general color tonality of the outer and inner petal surfaces, respectively, which remains constant from the opening bud stage throughout the life of the flowers, including the dehydrated petal stage even when cut from the plant, and exceptionally good keeping qualities of the flowers.

No references cited.